United States Patent
Morris et al.

(10) Patent No.: US 7,633,062 B2
(45) Date of Patent: Dec. 15, 2009

(54) RADIATION PORTAL MONITOR SYSTEM AND METHOD

(75) Inventors: Christopher Morris, Los Alamos, NM (US); Konstantin N. Borozdin, Los Alamos, NM (US); J. Andrew Green, Los Alamos, NM (US); Gary E. Hogan, Los Alamos, NM (US); Mark F. Makela, Los Alamos, NM (US); William C. Priedhorsky, Los Alamos, NM (US); Alexander Saunders, Los Alamos, NM (US); Larry J. Schultz, Los Alamos, NM (US); Michael J. Sossong, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 363 days.

(21) Appl. No.: 11/771,169

(22) Filed: Jun. 29, 2007

(65) Prior Publication Data

US 2008/0191133 A1 Aug. 14, 2008

Related U.S. Application Data

(60) Provisional application No. 60/855,064, filed on Oct. 27, 2006.

(51) Int. Cl.
*G01N 23/00* (2006.01)
*G01N 23/201* (2006.01)

(52) U.S. Cl. .................. 250/308; 250/306; 250/307; 250/370.03; 250/370.09; 250/370.11; 378/4; 378/21; 378/22

(58) Field of Classification Search ......... 250/306–308, 250/336.1, 370.01, 370.02, 370.03, 370.09, 250/370.11, 372–375, 388, 389, 472.1, 473.1; 378/1, 4, 6, 8, 9, 21, 24–27, 29, 45, 53, 54, 378/63, 83, 85, 86, 88; 340/600, 629, 815.4; 73/170.27
See application file for complete search history.

(56) References Cited

U.S. PATENT DOCUMENTS 5,851,182 A * 12/1998 Sahadevan .................. 600/407

(Continued)

OTHER PUBLICATIONS

Radiographic Imaging with Cosmic-Ray Muons; K.N. Borozdin, G.E. Hogan, C. Morris, W.C. Priedhorsky, A. Saunders, L.J. Schultz, M.E. Teasdale; Los Alamos National Laboratory; vol. 422, Mar. 20, 2003, www.nature.com/nature.

(Continued)

*Primary Examiner*—Bernard E Souw
(74) *Attorney, Agent, or Firm*—Matthew F. Lambrinos; Kermit D. Lopez; Luis M. Ortiz (57) ABSTRACT

A portal monitoring system has a cosmic ray charged particle tracker with a plurality of drift cells. The drift cells, which can be for example aluminum drift tubes, can be arranged at least above and below a volume to be scanned to thereby track incoming and outgoing charged particles, such as cosmic ray muons, whilst also detecting gamma rays. The system can selectively detect devices or materials, such as iron, lead, gold and/or tungsten, occupying the volume from multiple scattering of the charged particles passing through the volume and can also detect any radioactive sources occupying the volume from gamma rays emitted therefrom. If necessary, the drift tubes can be sealed to eliminate the need for a gas handling system. The system can be employed to inspect occupied vehicles at border crossings for nuclear threat objects.

20 Claims, 12 Drawing Sheets

U.S. PATENT DOCUMENTS

| | | | |
|---|---|---|---|
| 7,064,336 B2* | 6/2006 | Archer et al. | 250/370.1 |
| 7,095,329 B2 | 8/2006 | Saubolle | 340/600 |
| 7,145,150 B2 | 12/2006 | Chugg | 250/370.01 |
| 7,279,676 B2* | 10/2007 | Twomey | 250/252.1 |
| 7,317,390 B2* | 1/2008 | Huey et al. | 340/552 |
| 7,470,905 B1 | 12/2008 | Goldberg et al. | |
| 2005/0023477 A1 | 2/2005 | Archer et al. | 250/370.11 |
| 2005/0029460 A1 | 2/2005 | Iwatschenko-Borho et al. | 250/359.1 |
| 2006/0145092 A1 | 7/2006 | Gunn et al. | 250/474.1 |
| 2006/0180753 A1 | 8/2006 | Bryman | 250/266 |
| 2007/0070231 A1 | 3/2007 | Hawes et al. | 348/311 |
| 2007/0102648 A1 | 5/2007 | Shpantzer et al. | |
| 2008/0191133 A1* | 8/2008 | Morris et al. | 250/307 |
| 2008/0228418 A1* | 9/2008 | Green | 702/81 |
| 2008/0265156 A1* | 10/2008 | Morris et al. | 250/305 |
| 2008/0303664 A1* | 12/2008 | Huey et al. | 340/552 |
| 2008/0315091 A1* | 12/2008 | Morris et al. | 250/307 |

OTHER PUBLICATIONS

Detection of High-Z Objects Using Multiple Scattering of Cosmic Ray Muons; W.C. Priedhorsky, K.N. Borozdin, G.E. Hogan, C. Morris, A. Saunders, L.J. Schultz, M.E. Teasdale; Review of Scientific Instruments, vol. 74, No. 10, Oct. 2003.

Cosmic Ray Muon Radiography; Larry J. Schultz; Dissertation for Ph.D. Electrical and Computer Engineering, Portland State University 2003.

Image Reconstruction and Material Z Discrimination Via Cosmic Ray Muon Radiography; L.J. Schultz, K.N. Borozdin, J.J. Gomez, G.E. Hogan, J.A. McGill, C.L. Morris, W.C. Priedhorsky, A. Saunders, M.E. Teasdale; NIM Submission Draft—Jun. 30, 2003.

Borozdin, Konstantin et al., "Cosmic-Ray Muon Tomography and Its Application to the Detection of High-Z Materials", Proceedings of the 46th Annual Meeting, Institute of Nucelar Materials Management, 2005, pp. 1-8.

Zhao, T. et al. "D0 Forward -Angle Muon Tracking Detector and Its Gas System", IEEE Transactions on Nuclear Science, Jun. 2002, vol. 49, No. 3 pp. 1092-1096.

Byrd, Roger C. et al. "Nuclear Detection to Prevent or Defeat Clandestine Nuclear Attack", IEEE Sensors Journal, Aug. 2005, vol. 5, No. 4, pp. 593-609.

Zhou, Bing, "Large Precision Muon Detector for ATLAS", Nuclear Instruments and Methods in Physics Research A, 2002, vol. 494, pp. 464-473.

Hengartner, Nicolas et al., Information Extraction for Muon Radiography, Nuclear Science Symposium Conference Record, 2005 IEEE, vol. 1, Oct. 23-29, 2005 pp. 11-15.

Fessler, Jeffery A. "Statistical Methods for Image Reconstruction" (annotated slides for attendees of the NSS-MIC short Course), Oct. 24, 2004.

Schultz, L. J. et al., "Image Reconstruction and Material Z Discrimination via Cosmic Ray Muon Radiography", Nuclear Instruments and Methods in Physics Research A, 2004, vol. 519, pp. 687-694.

Jenneson, P.M. "Large Vessel Imaging Using Cosmic-ray Muons", Nuclear Instruments and Methods in Physics Research A, 2004, vol. 525, pp. 346-351.

Fessler, Jeffery A., "Penalized Maximum-Likelihood Image Reconstruction Using Space-Alternating Generalized EM Algorithms", IEEE Transactions on Image Processing, 1995, vol. 4 No. 10, pp. 1417-1429.

PCT—Notification of Transmittal of the International Search Report and the Written Opinion of the International Searching Authority, or the Declaration, Date of Mailing, Dec. 24, 2008.

Gene R. Kelley, "A Terrorist Threat—The Movement of Black Market Nuclear Materials into the United States", Nov. 17, 2001, Nuclear Age Peace Foundation.

* cited by examiner

| MATERIAL | dE/dx<br>MeV-cm²/gm | $\chi$<br>cm |
|---|---|---|
| $H_2O$ | 2.06 | 36 |
| Fe | 1.87 | 1.76 |
| Pb | 1.54 | 0.56 |

RADIATION PORTAL MONITOR SYSTEM AND METHOD

CROSS-REFERENCE TO PROVISIONAL APPLICATION

This application claims priority under 35 U.S.C. § 119(e) to U.S. Provisional Patent Application Ser. No. 60/855,064, entitled "Systems, Methods and Apparatus for Particle Detection and Analysis and Field Deployment of the Same", which was filed on Oct. 27, 2006, the disclosure of which is incorporated herein by reference.

STATEMENT REGARDING FEDERAL RIGHTS

This invention was made with Government support under Contract Number DE-AC52-06NA25396 awarded by the United States Department of Energy. The Government has certain rights in the invention.

TECHNICAL FIELD

Embodiments relate to fields of particle detection, analysis, control and, more particularly but not exclusively, to portal monitoring systems and methods.

BACKGROUND

The threat of the detonation of a nuclear device in a major US city has prompted research aimed at providing more robust border surveillance for contraband nuclear material.

An article entitled "A Terrorist Threat—The movement of Black Market Nuclear Materials into the United States" dated November 2001 in the name of Gene R. Kelley from the article archives of the Nuclear Age Peace Foundation, PMB 121, 1187 Coast Village Road, Suite 1, Santa Barbara, Calif. 93108, USA, outlines the problem of surreptitious transport of special nuclear material. Kelly refers to some possibilities for moving this type of material as being as follows:
  1)—superimpose the shipment of small, well-shielded packages on established drug and contraband routes.
  2)—ship materials conventionally in well shielded, small containers through a surreptitiously network of widely dispersed handlers.
  3)—man carrying many small quantities across the mostly porous borders of the United States.
  4)—use diversified distribution techniques (routes and conveyances) by requiring multiple way-points and altering the characteristics of external shipping containers at each point.
  5)—mix materials and legitimate products for routine deliveries.

Kelley concludes that the formidable nature of the tasks required to detect and identify well packaged fissile materials renders the likelihood of detection in small quantities highly questionable.

The use of portal monitors at border crossing points is becoming routine for detecting smuggled nuclear materials. In many cases shielding can be used to obscure a nuclear signature. Conventional nuclear material detectors use high resolution gamma or X ray detectors.

Figure 1:
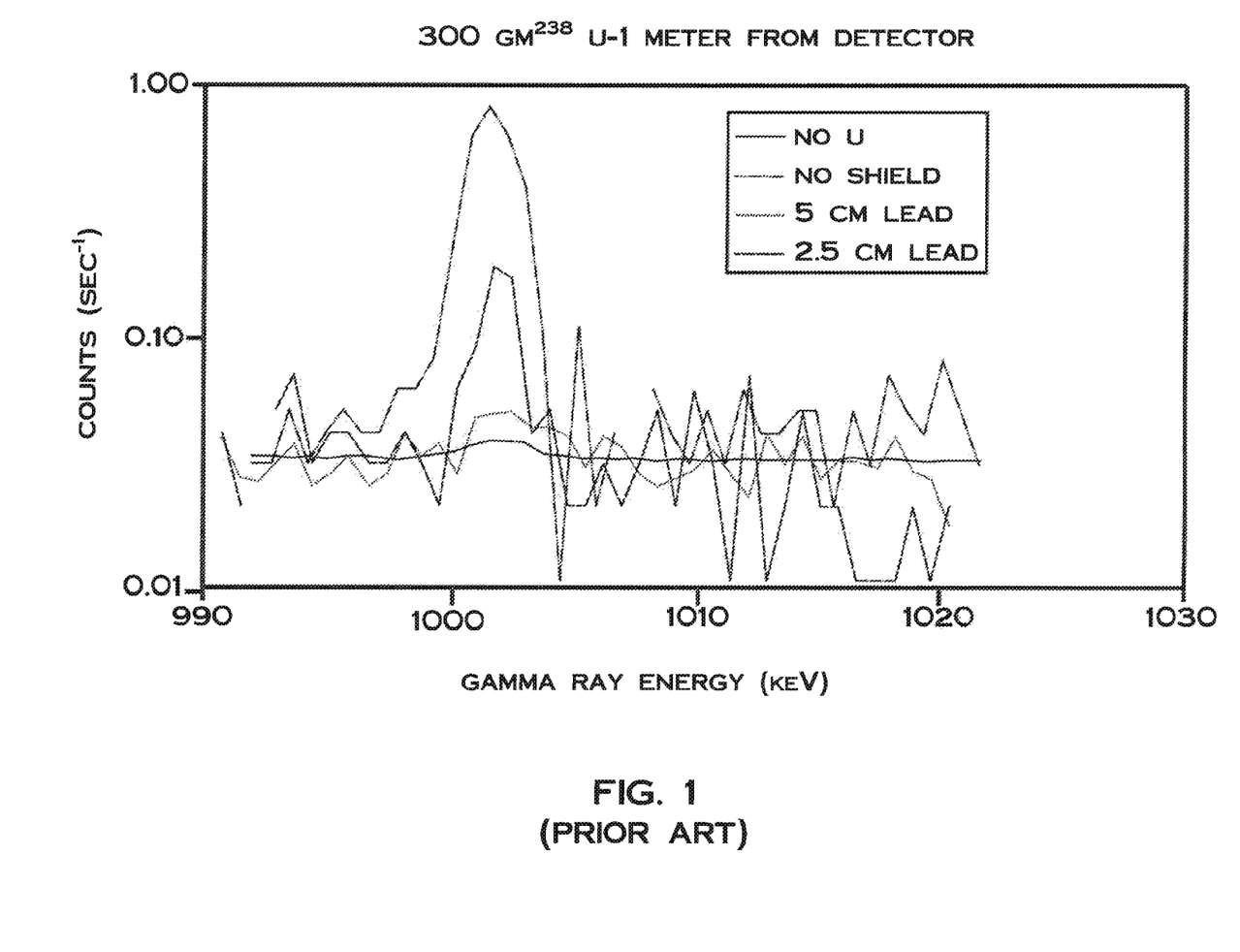
FIG. 1 illustrates example count data from a high resolution gamma ray detector used to detect Weapon grade uranium (WGU): 10% 238 U 90% 235 U, using the gamma-ray signal from a 400 gm sample of 238 U, without shielding and with 5 cm and 2.5 cm of lead shielding, respectively.

Unshielded Kg quantities of highly enriched uranium can be detected with high reliability with 1 minute counting times by detecting gamma rays from the 238 U impurity. FIG. 1 of the accompanying drawings depicts example count data from a high resolution gamma ray detector used to detect Weapon grade uranium (WGU): 10% 238 U 90 % 235 U without shielding and with 5 cm and 2.5 cm of lead shielding, respectively. FIG. 1 indicates how self-shielding of nuclear material reduces count rates. In order to shield a threat object, about 5 cm thick lead, gold, tungsten, or other shielding material is required.

Figure 2:
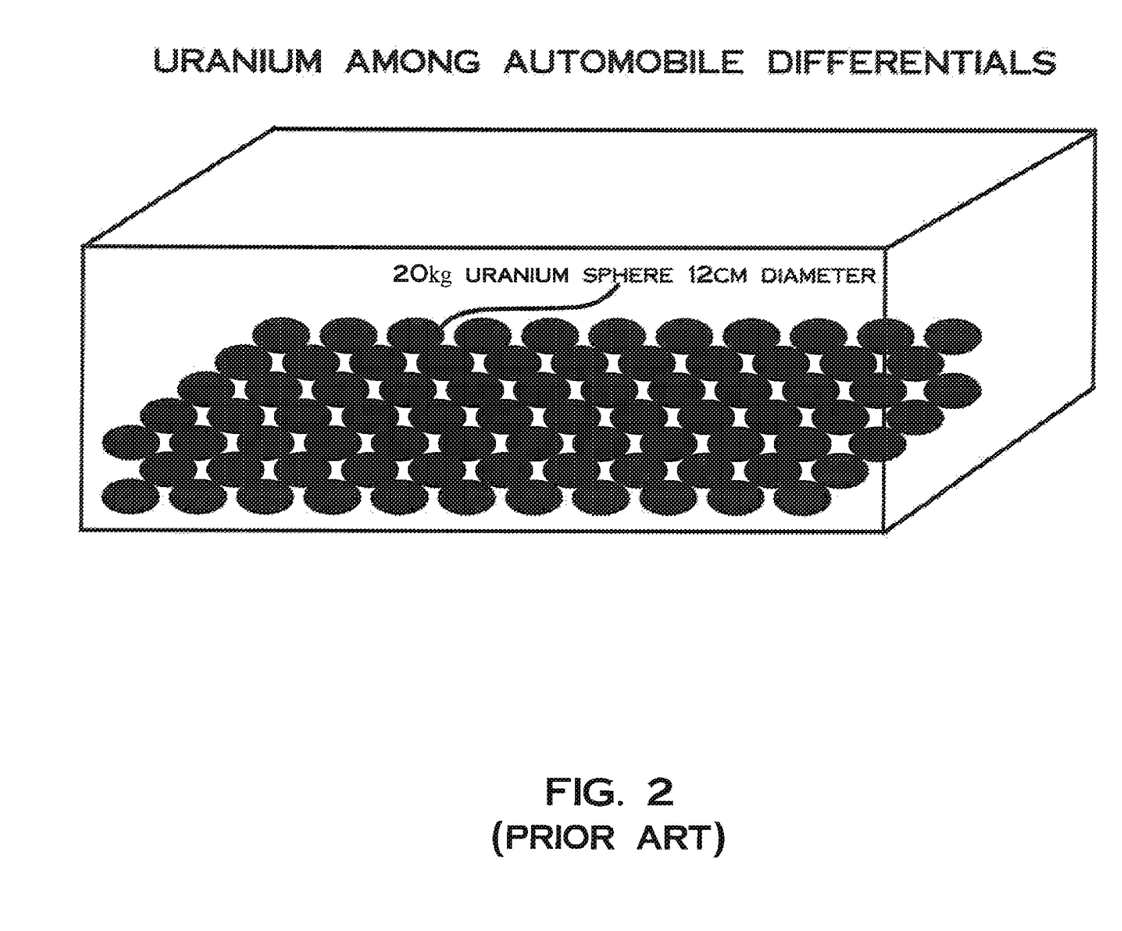
Figure 3:
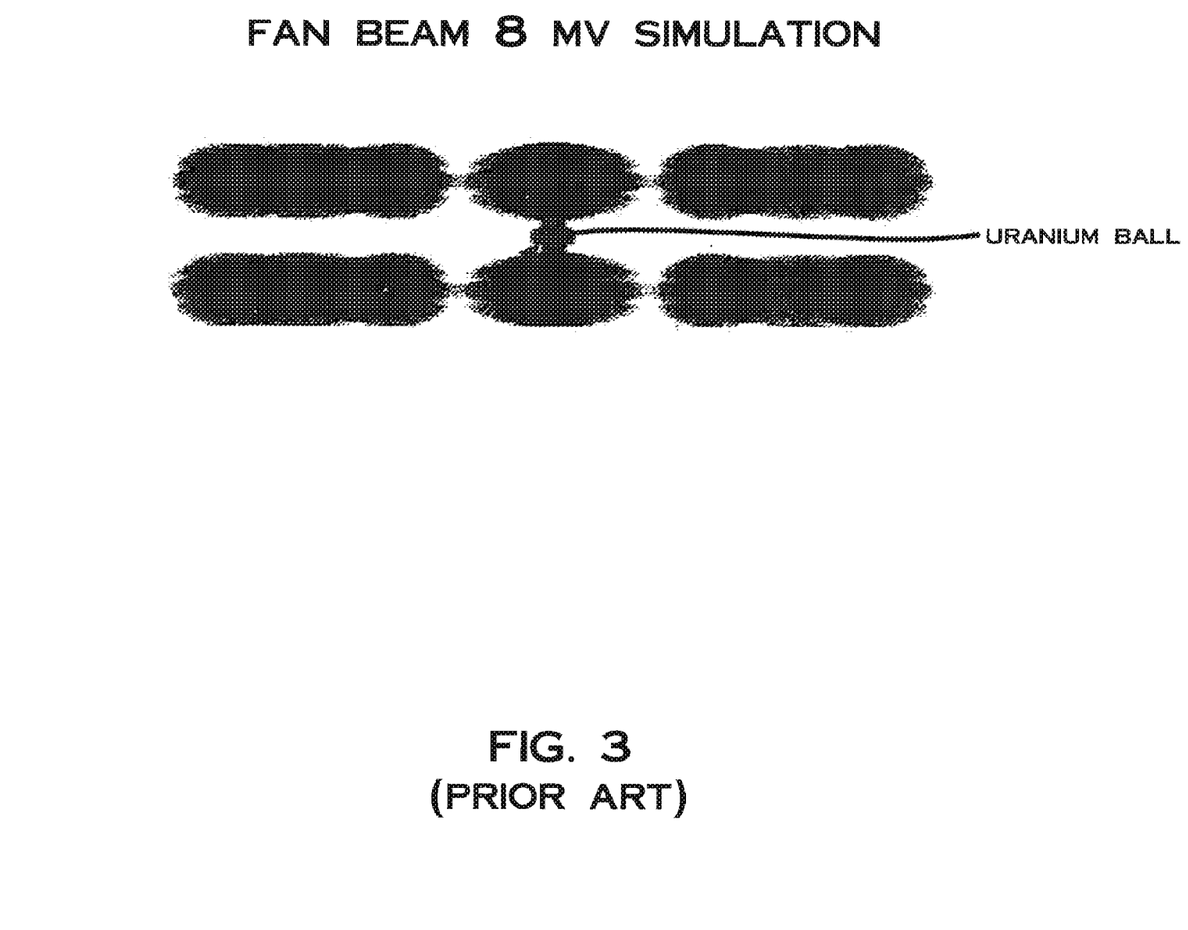

As indicated by FIG. 1 and additionally FIGS. 2 and 3, which illustrate simulations of X-radiography of 20 kg of uranium among automobile differentials using a fan beam of x-rays generated by 8 MV electron bhemstralung source. These simulations show that X-ray radiography can visualize objects, even in some dense, cluttered cargo, but definitive signatures of high z objects are confused by scatter backgrounds and transmission is insufficient for many cargos.

Having regard to the foregoing, the small amount of material needed to construct a nuclear device and the ease with which neutron and gamma ray signatures can be obscured with shielding makes robust border surveillance for contraband nuclear material difficult.

BRIEF SUMMARY

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

The aforementioned aspects of the invention and other objectives and advantages can now be achieved as described herein.

According to one aspect, a portal monitoring system has a cosmic ray charged particle tracker with a plurality of charged particle detectors. The charged particle detectors are in the form of drift cells, which can be for example drift tubes of circular or non-circular cross section or non-tube shaped cells, configured both to enable tracking of incoming and outgoing charged particles passing through a volume to be scanned, such as cosmic ray muons, and detection of gamma rays. The system can both selectively detect devices or materials, particularly but not exclusively high density materials such as iron, lead, gold and/or tungsten, occupying the volume from multiple scattering of the charged particles passing through the volume and detect radioactive sources occupying the volume from gamma rays emitted therefrom.

Advantageously, adopting drift cells as charged particle detectors in the cosmic ray tracker effectively provides the combined function of a cosmic ray radiography apparatus with a gamma radiation counter to provide a robust detector for nuclear threats. This eliminates the need for two separate instruments.

The drift cells can be sealed drift cells further reducing the cost and complexity of the system by eliminating the need for a gas handling system.

A typical operating gas of the drift tubes comprises a non-flammable gas, such as a mixture of argon, carbon dioxide and Tetrafluoromethane ($CF_4$).

The drift cells can comprise a set of drift tubes located above the volume and another set of drift tubes located below the volume. Each set of drift tubes can have at least three drift tubes configured in a first direction and another at least three drift tubes configured in a second direction. The first direction can be orthogonal to the second direction.

A gamma ray or neutron source can be arranged within the system to enable active interrogation of material occupying the volume.

According to another aspect, a portal monitor system has a cosmic muon tracker having a plurality of muon detectors in the form drift cells. The drift tubes can be arranged at least above and below a volume to be scanned both to enable tracking of incoming and outgoing muons and counting of gamma rays. In use, the system can both selectively detect high density shielding of radioactive material occupying the volume from multiple scattering of the muons passing through the volume and detect the radioactive material occupying the volume from gamma rays emitted therefrom.

The volume to be scanned can be of sufficient size to enable a vehicle or cargo container to occupy the volume. Advantageously, adopting drift tubes as muon detectors enables the system to perform passive scanning of occupied passenger vehicles with short scanning times and no dose radiation above ambient background.

According to yet another aspect, a method of portal monitoring comprises arranging a plurality drift cells on opposite sides of a volume to be scanned; detecting with the drift cells incoming and outgoing cosmic ray charged particles together with any gamma rays; selectively detecting any material occupying the volume from multiple scattering of the charged particles passing through the volume; and detecting from the gamma rays any radioactive sources occupying the volume.

Arranging the plurality of drift cells can comprise arranging a set of at least three planes of drift tubes above the volume and arranging a set of at least three planes of drift tubes below the volume and can further comprise arranging the drift tubes in each plane in two orthogonal coordinates.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIGS. 2 and 3, 1 (Prior Art) illustrate X-ray radiography simulations of uranium detection among automobile differentials and a fan beam 8 MV;

DETAILED DESCRIPTION

The particular values and configurations discussed in these non-limiting examples can be varied and are cited merely to illustrate at least one embodiment of the present invention and are not intended to limit the scope of the invention.

The portal monitoring system according to the illustrative embodiments provides an approach to enable robust nuclear material detection at reduced cost and with increased effectiveness. Furthermore, the approach can provide a radiation portal monitor which is capable of determining if a given vehicle or cargo is free of nuclear threats by both measuring the absence of a potential shielded package and the absence of a radiation signature.

The portal monitoring systems of the illustrative embodiments shown in the accompanying drawings employ cosmic ray charged particle tracking with drift tubes. As will be explained in more detail below, the portal monitoring systems utilize drift tubes to enable tracking of charged particles, such as muons, passing through a volume as well as detection of gamma rays. Advantageously, these portal monitoring systems can effectively provide the combined function of a cosmic ray radiography apparatus with passive or active gamma radiation counter to provide a robust detector for nuclear threats. This eliminates the need for two separate instruments.

Cosmic ray tomography is a technique which exploits the multiple Coulomb scattering of highly penetrating cosmic ray muons to perform non-destructive inspection of the material without the use of artificial radiation. The Earth is continuously bombarded by energetic stable particles, mostly protons, coming from deep space, these particles interact with atoms in the upper atmosphere to produce showers of particles that include many short-lived pions which decay producing longer-lived muons. Muons interact with matter primarily through the Coulomb force having no nuclear interaction and radiating much less readily than electrons. They lose energy only slowly through electromagnetic interactions. Consequently, many of the muons arrive at the Earth's surface as highly penetrating charged radiation. The muon flux at sea level is about 1 muon per $cm^2$ per minute.

As a muon moves through material, Coulomb scattering off of the charges of sub-atomic particles perturb its trajectory. The total deflection depends on several material properties, but the dominant effect is the atomic number, Z, of nuclei. The trajectories are more strongly affected by materials that make good gamma ray shielding (lead and tungsten) and by special nuclear material (SNM), that is, uranium and plutonium, than by materials that make up more ordinary objects such as water, plastic, aluminum and steel. Each muon carries information about the objects that it has penetrated, and by measuring the scattering of multiple muons one can probe the properties of these objects. In particular, one can detect high density, that is, high Z, objects, inside low-Z and medium-Z matter.

Coulomb scattering from atomic nuclei results in a very large number of small angle deflections of charged particles as the transit mailer. Enrico Fermi found and solved a transport equation that describes this process to a good approximation. The result is a correlated Gaussian distribution function for the displacement and angle change of the trajectory that depends on the density and the atomic charge of the material. The width of the distribution function is proportion to the inverse of the momentum of the particle and the square root of the real density of material measured in radiation lengths. Further background can be found in the reference of K. N. Borozdin et al entitled "Surveillance: Radiographic Imaging with Cosmic Ray Muons", published in Nature (2003), 422,277.

Cosmic ray muons can provide information with no radiation dose above background and is especially sensitive to good shielding materials. The system can be configured to perform tomography to localize scattering (RC and LS). The tomographic position resolution can be expressed approximately as follows:

$$\Delta x = \theta_{RMS} L \qquad \text{Eq. 1}$$

where:

$\theta_{RMS}$=the scattering angle rms, and

L=the size of the apparatus

For example, for a typical scattering angle of 0.02 and an apparatus size of 200 cm, the tomographic position resolution is 0.02×200 cm=4 cm.

Poisson statistics determine the density sensitivity according to the equation:

$$\frac{\Delta \theta}{\theta} = \frac{1}{\sqrt{2N}} \qquad \text{Eq. 2}$$

where:

θ=the rms scattering angle,

N=number of cosmic rays

For example, the density resolution for N=100/min of a 10×10 cm$^2$ $^{object}$ can be expressed as Δθ=0.07θ after one minute of counting.

Figure 10:
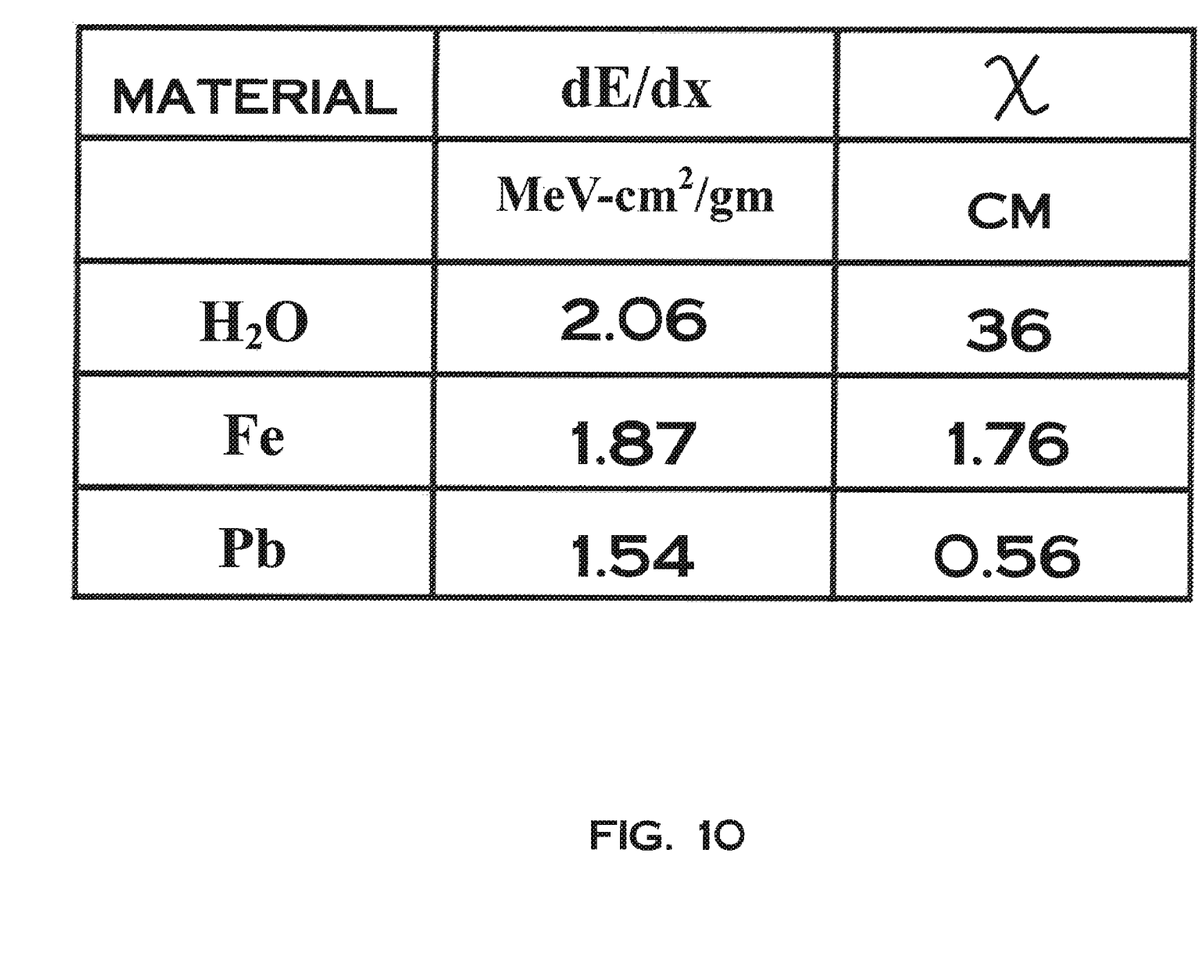
FIG. 10 depicts a table showing theoretical energy loss rate (dE/dx) and radiation length (X) for various material.

Referring to the table of FIG. 10, this table illustrates theoretical energy loss rate (dE/dx) and radiation length (X) for various materials. One minute of counting distinguishes a 10 cm cube of iron from a 10 cm cube of lead at 6 standard deviations.

Tomographic methods, generally used to construct an image or model of an object from multiple projections taken from different directions, can be implemented in the cosmic ray system to provide a discrete tomographic reconstruction of the volume of interest based on the data provided by the muons. Monte Carlo simulation techniques can be used to study applications and shorten scanning times.

Figure 4:
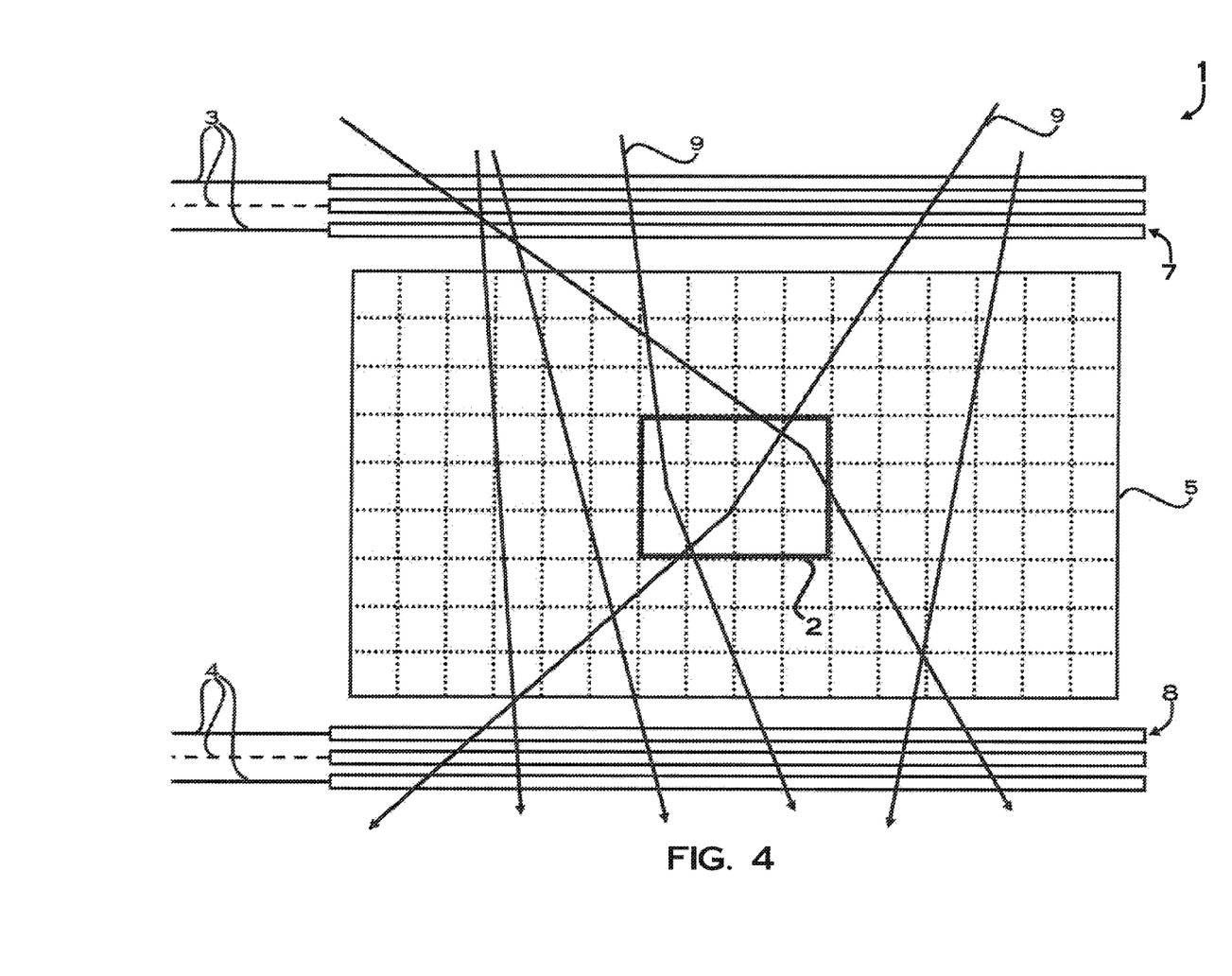
FIG. 4 illustrates a portal monitoring system utilizing cosmic rays to detect an object according to one embodiment.
Figure 5:
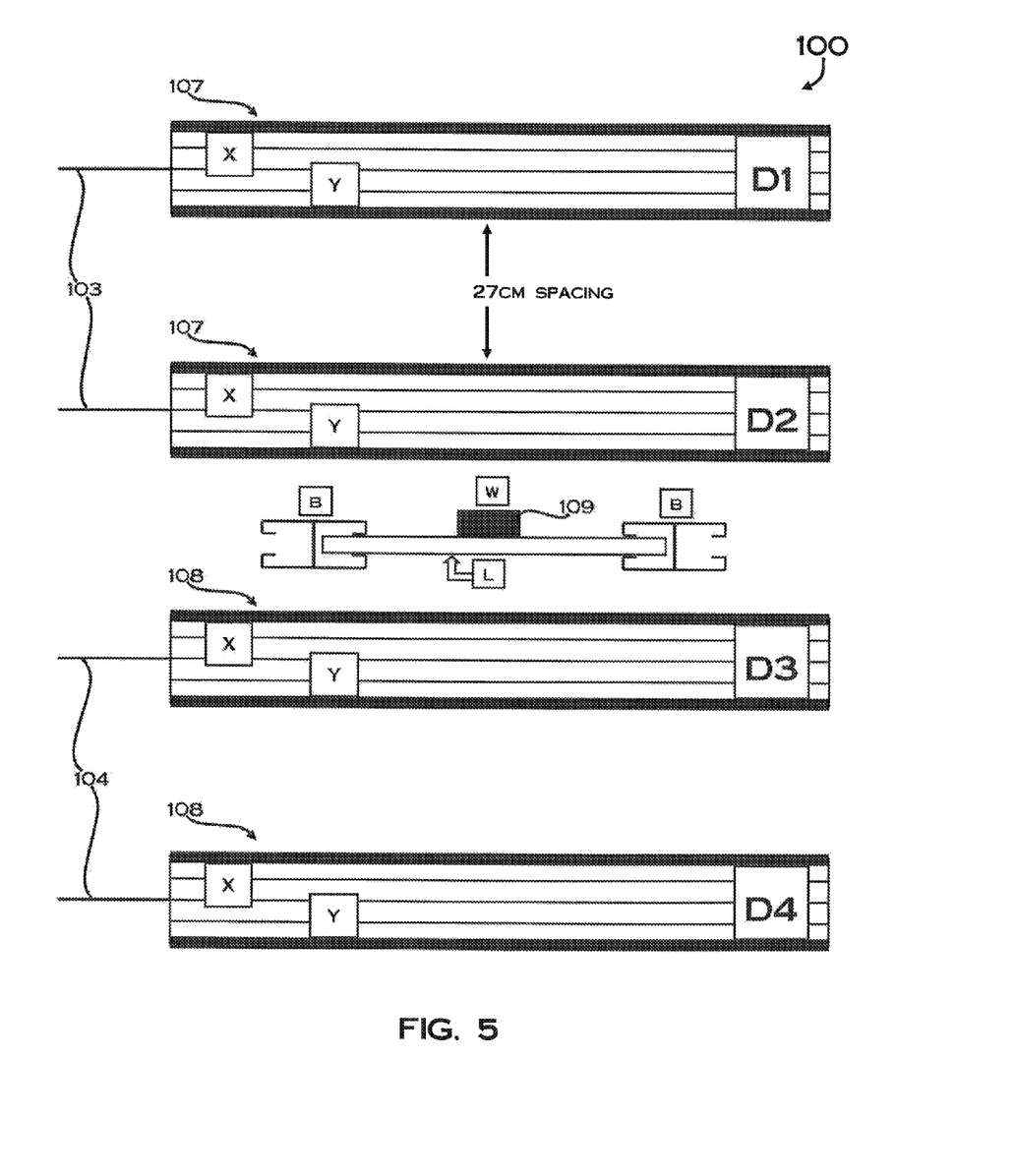
FIG. 5 illustrates a side view of another portal monitoring system utilizing cosmic rays to detect an object according to another embodiment.
Figure 6:
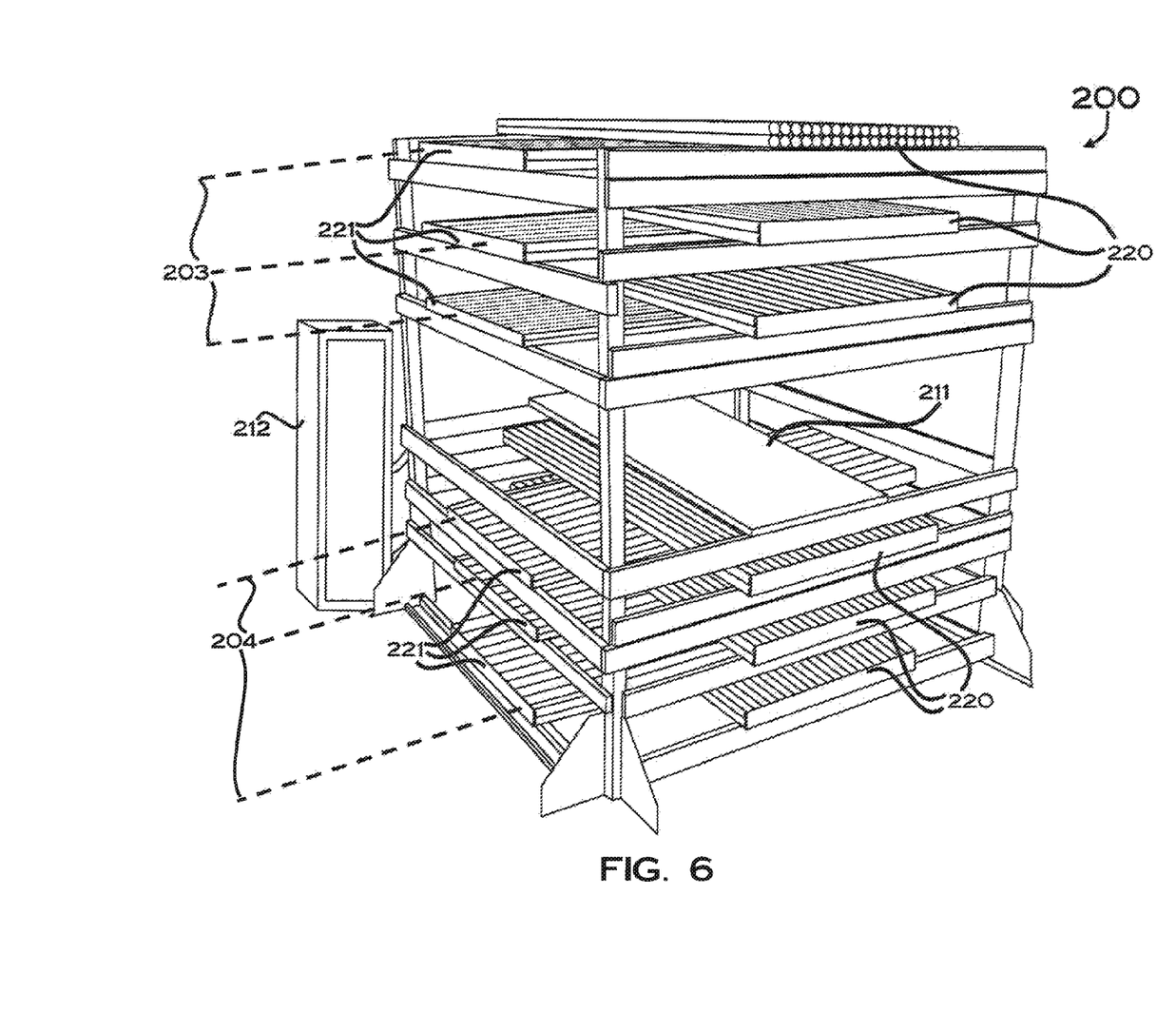
FIG. 6 illustrates a detailed perspective view of a portal monitoring system according to a preferred embodiment.

The cosmic ray radiography function of the portal monitoring systems of the embodiments can be more readily understood with reference to exemplary portal monitoring systems such as those shown in FIGS. 4-6. Referring initially to FIG. 4, which illustrates a portal monitoring system utilizing cosmic rays to detect an object, system 1 has a set of two or more planes 3 of position muon detectors 7 arranged above a volume 5 to be imaged for providing the position and angle of incoming muon tracks 9. The muon detectors 7 are configured to measure the position and angle of incoming muon tracks 9 in two orthogonal coordinates. Muons pass through the volume 5 and are scattered to an extent dependent upon the material 2 occupying the volume through which they pass. Another set of two or more planes 4 of muon detectors 8 are configured to record outgoing muon positions and angles. Side detectors (not shown) may be used to detect more horizontally orientated muon tracks. The scattering angle of each muon is computed from the incoming and outgoing measurements.

Thus, multiple scattering of cosmic ray muons can be used to selectively detect high z-material in a background of normal cargo. Advantageously, this technique is passive, does not deliver any radiation dose above background, and is particularly selective to high-z dense materials.

Referring to FIG. 5, which illustrates a side view of another portal monitoring system utilizing cosmic rays to detect an object according to another embodiment, the system 100 has two planes 103 of muon detectors 107 located above the sample 109 and two planes 104 of muon detectors 108 located below the sample 109. In the system 100 the planes of muon detectors are separated by 27 cm spacings but other spacings are possible.

In a preferred embodiment of the portal monitoring system, the muon tracking detectors are configured to enable passive gamma ray counting while they are being used for cosmic ray muon tracking. FIG. 6 illustrates a detailed perspective view of a portal monitoring system 200 according to a preferred embodiment in which a set of three planes 203 of muon detectors are arranged above the sample holder plane 211 and a set of three planes 204 of muon detectors are arranged below the sample holder plane 211. The muon detectors are in the form of X coordinate drift tube modules 221 and Y coordinate drift tube modules 220 which are operable to detect both cosmic ray muons and gamma rays. In the embodiment of FIG. 6, the drift tube modules are 12 foot long aluminum drift tubes which are configured to measure the position and angle of incoming and outgoing muon tracks in Y and X coordinate directions. In each of the X and Y directions of each plane 203, the drift tubes are arranged in two rows offset by half a tube diameter from each other.

Whilst in the illustrative embodiment of FIG. 6, the X and Y direction drift tubes are arranged in three separate planes above and below the volume to be scanned, the drift tubes can have any configuration above and below the volume to be scanned that enables them to make three measurements in the X-Y directions or other two orthogonal directions. To this end, each set of drift tubes located above and below the volume to be scanned need only have at least three drift tubes configured in a first direction and another at least three drift tubes configured in a second direction orthogonal to the first direction.

The aluminum in the detectors provides a considerable amount of mass in which gamma rays are absorbed of scattered. The energetic electrons produced in these processes are detected locally in the drift tubes in the same way that more energetic cosmic rays are detected. Data acquisition electronics 212 are operably coupled to the drift tubes.

Advantageously, system 200 can selectively detect high density shielding of radioactive material occupying the volume from multiple scattering of the cosmic ray muons whilst also counting gamma rays emitted from the radioactive material. In addition to detecting high density materials, such as lead, gold, tungsten, uranium and plutonium, the system can be employed to detect medium density materials, such as steel, iron and copper, and also low density materials, such as water, plastic, concrete and aluminum, albeit with a somewhat lower accuracy than for high density materials.

Figure 7:
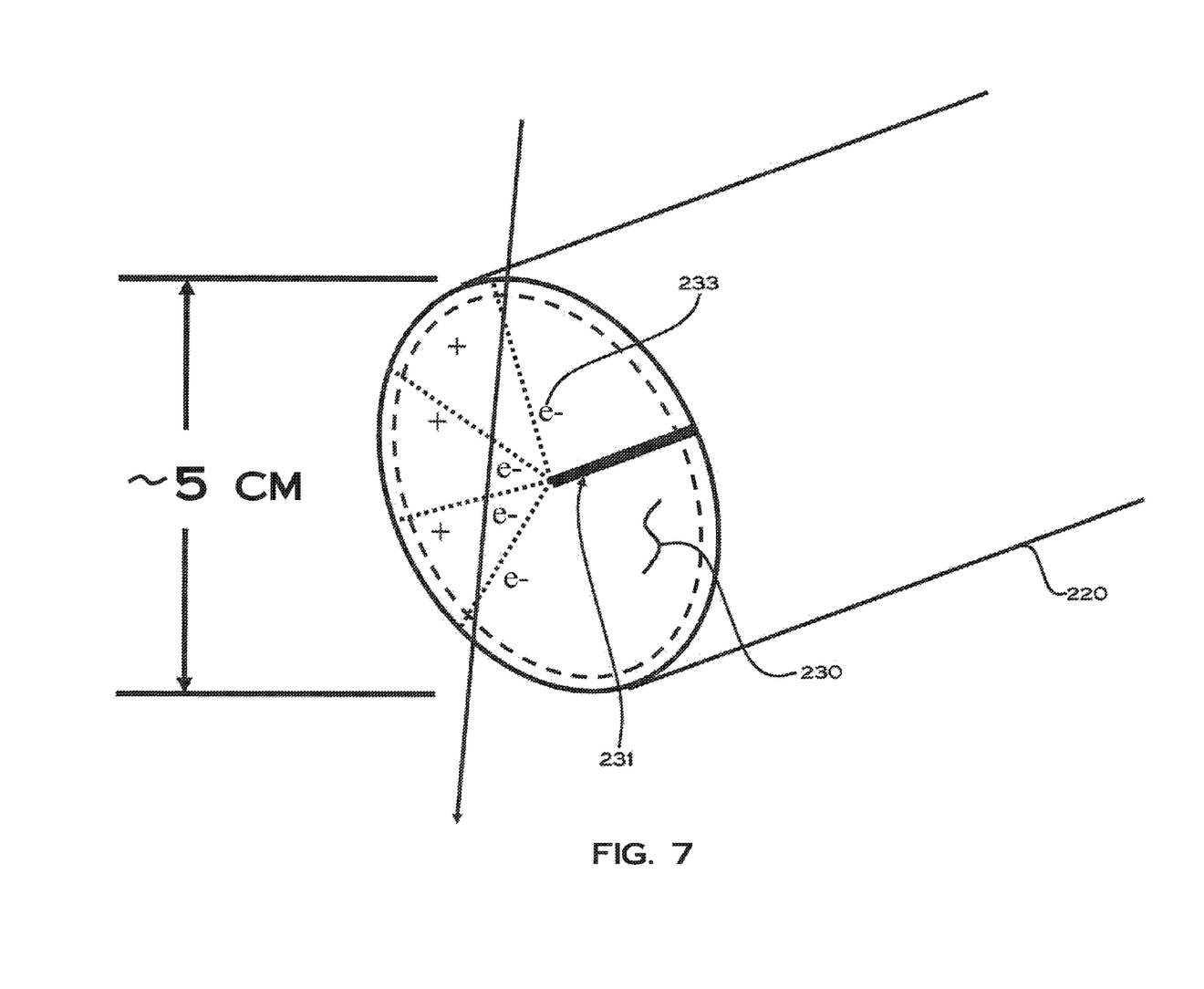
FIG. 7 illustrates a cross-sectional view of part of a drift tube module configured to detect cosmic ray charged particles and gamma rays according to one embodiment.

A cross-sectional view of part of a typical drift tube module 220 is illustrated in FIG. 7. The drift tube module is typically cylindrical and filled with a detector gas such as argon-isobutane 230 to enable detection of the cosmic ray charged particles, such as muons. The system is configured to apply a positive HV of about +2-3 kV to a central anode wire 231 extending along the length of the cylindrical tube with the tube at ground so that a high-voltage static field is also present. When the charged particle interacts with gas atoms, many electrons 233 are liberated from those atoms in a straight line through a chord of the tube. The static field causes the "string" of electrons to drift toward the positively charged anode wire which is read-out electronically with TDCS (time-to-digital converters) of the data acquisition electronics 212.

Whilst in the drift tube of the illustrative embodiment of FIG. 7, the detector gas is argon-isobutane 230; other operating gas mixtures may be argon/carbon dioxide or argon/isobutane/carbon dioxide. Furthermore, non-flammable gas mixtures such as argon-carbondioxide-tetrafluoromethane ($CF_4$) may alternatively be employed as the operating gas. Also, ethane or other gases may also be adopted in the gas mixtures. For example, a mixture of 5% ethane, 45% CF4 and 50% argon is a suitable non-flammable operating gas.

Also, whilst the drift tube of FIG. 7 is manufactured from aluminum, other materials such as carbon composite with internal conductive coatings can be adopted instead of aluminum. The drift tubes need not have circular cross-sections. For example, the drift tubes may be constructed from aluminum extrusions with multiple, non-circular cross-sections.

Alternatively, drift cells other than drift tubes can be adopted, such as for example triangular shaped drift cells.

Figure 8:
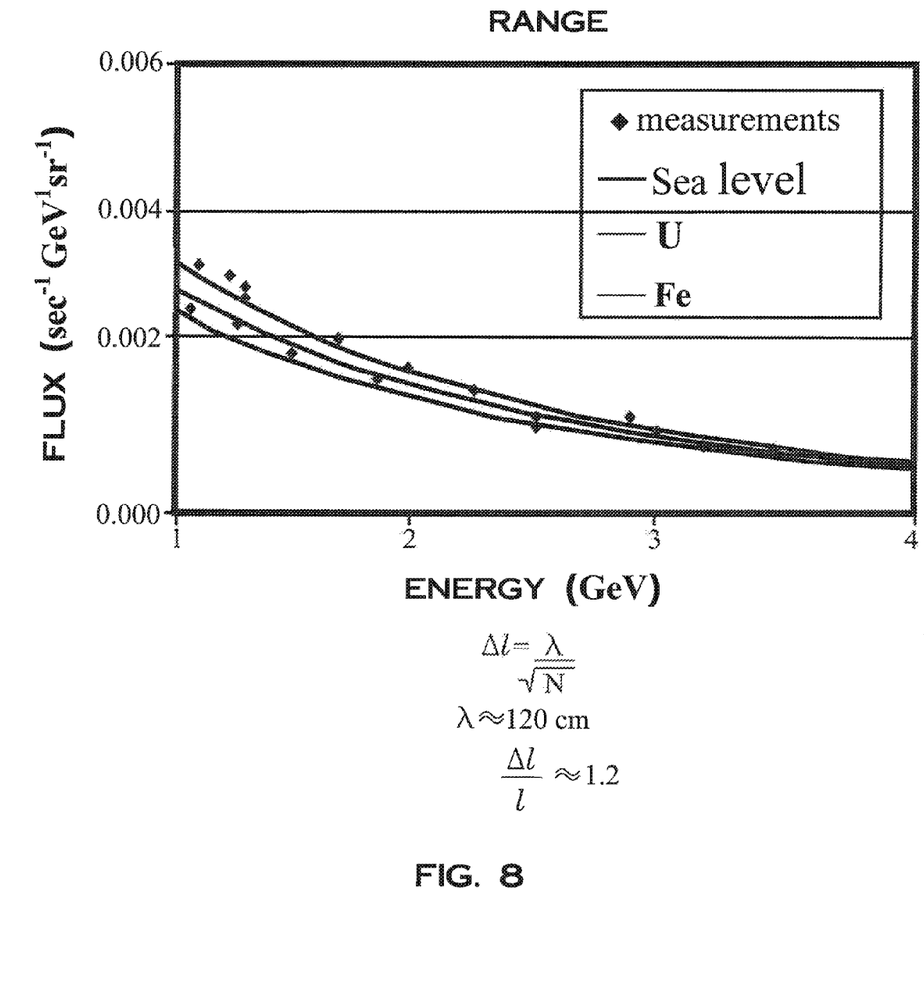
FIGS. 8 and 9 respectively illustrate typical experimental range data and multiple coulomb scattering theoretical results of measuring 1000 $cm^2$ of uranium for 1 minute with a cosmic ray system.
Figure 9:
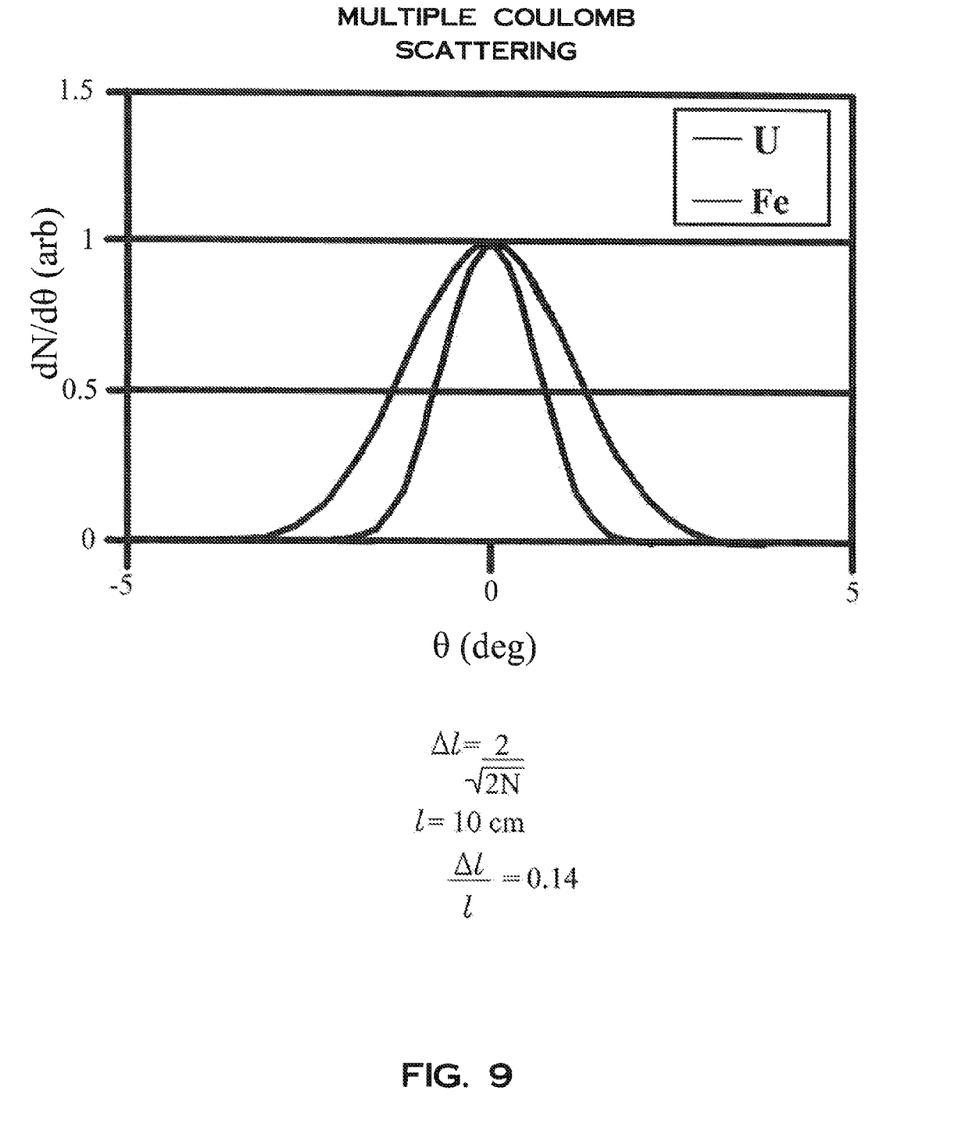

FIGS. 8 and 9, which respectively illustrate typical experimental range data and multiple coulomb scattering theoretical results of measuring 1000 $cm^3$ of uranium for 1 minute with a cosmic ray system, demonstrate that charged particle radiography is much more sensitive than range radiography.

Figure 11:
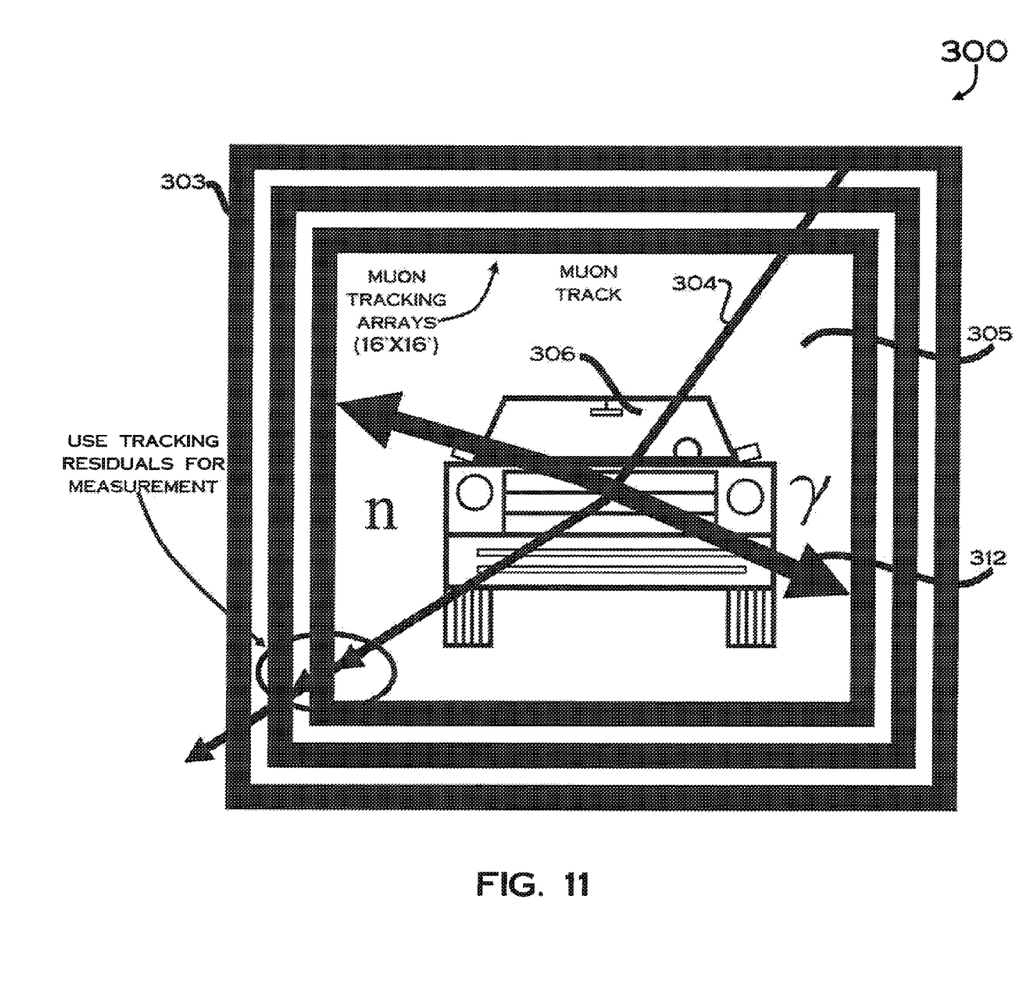
FIGS. 11 and 12 illustrate portal monitoring systems adapted and arranged to monitor cargo in vehicles and containers according to alternative embodiments.

Referring now to FIG. 11, which illustrates a portal monitoring system adapted and arranged to monitor cargo in vehicles and containers according to another preferred embodiment, the portal monitoring system 300 uses a muon tomography system with a plurality of detector drift tubes 303 configured to track cosmic ray muons scattered by the cargo or contents of a vehicle 306 occupying the volume 306 and configured to detect any gamma rays 312 emitted from the contents. The plurality of detector drift tubes 300 can be similar to the drift tubes 200, 221 of the system 200 of FIG. 6 and can be configured in an analogous manner. The system 300 can be employed for inspecting occupied vehicles at border crossings for nuclear threat objects which might range from fully assembled nuclear weapons to small quantities of highly shielded nuclear materials. The system 300 aims to pass innocent vehicles in less than 30 seconds, detect several Kgs of highly enriched uranium (HEU) in less than 60 seconds (shielded or unshielded) and detect plutonium or HEU nuclear devices in less than 60 seconds (shielded or unshielded).

Advantageously, using the drift tubes 303 to both passively count gamma radiation 312 emitted from the vehicle 306 and track the scattered cosmic ray charged particles 304 enables the system to perform passive scanning of occupied passenger vehicles with short scanning times and no dose radiation.

A method of operating the portal monitoring system 300 of FIG. 11 according to one embodiment involves detecting with the drift tubes 303 incoming and outgoing cosmic ray charged particles 304 together with any gamma rays 312. The multiple scattering of the charged particles are then computed to selectively detect any material, particularly high density material, occupying the volume 305. Any gamma rays 312 emitted from the volume are counted by the data acquisition electronics (not shown) to detect if any radioactive source is occupying the volume 305.

In an alternative embodiment, a portal monitoring system (not shown) is provided which is identical to that of the portal monitoring system 300 of FIG. 11 with the exception that the system also includes a gamma ray or neutron source within the apparatus to enable active rather than only passive interrogation of the vehicle and thereby provide a detectable increase in the gamma ray counting rate.

Figure 12:
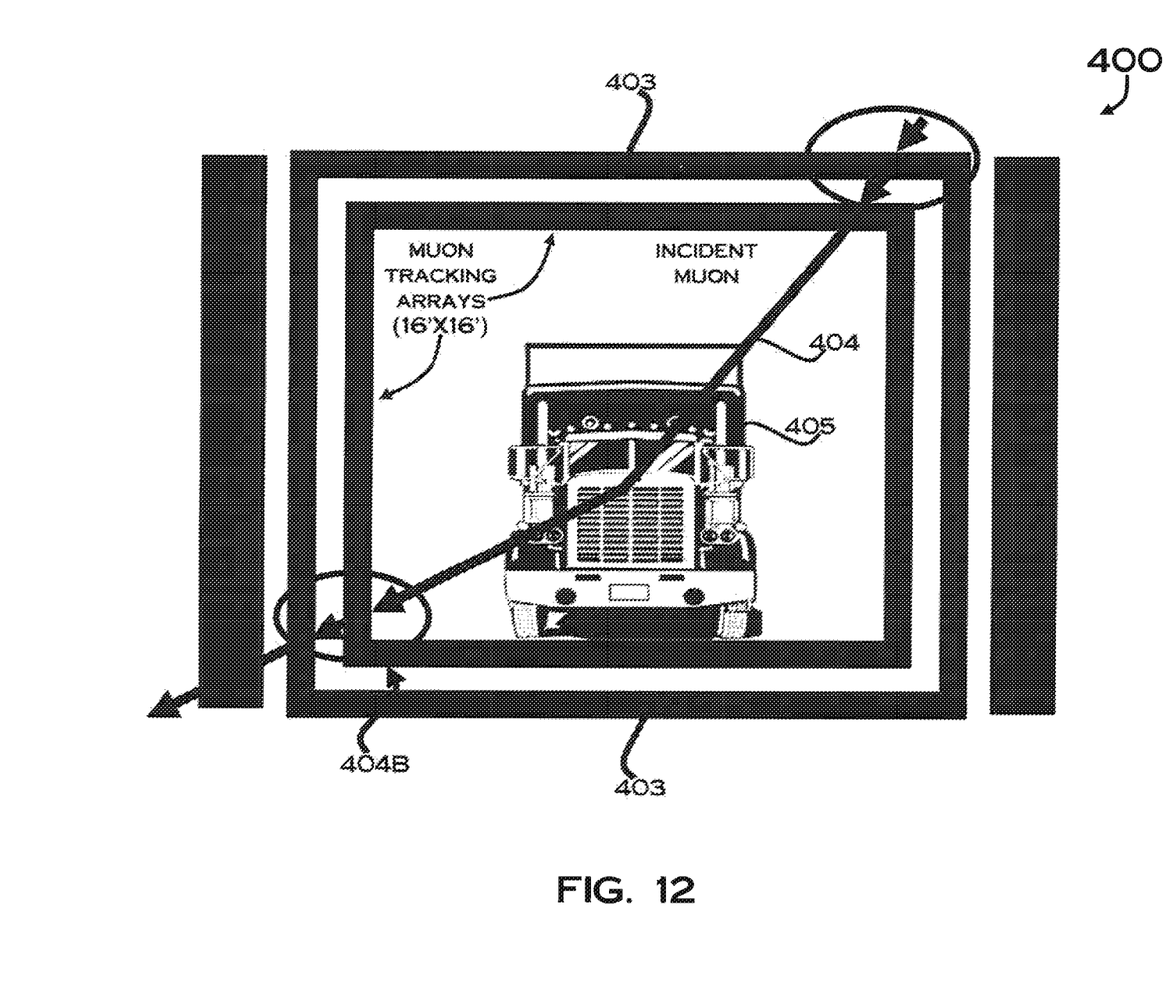

A portal monitoring system according to another alternative embodiment is illustrated in FIG. 12. System 400 is similar to the system 300 of FIG. 11 in that it is configured to both passively count gamma radiation emitted from the vehicle and track the scattered cosmic ray charged particles 404. The drift tube detectors arrays 403 are 16 foot long to enable interrogation of a truck 405 but may be other lengths dependent on the object being scanned. In order to obtain major gains in rate, the solid angle can be increased by filling out the drift tube detectors 403. Also, the system is configured to increase cosmic ray tracking efficiency by adjusting $(\epsilon^8)^2$ vs $(\epsilon^9+9(1-\epsilon)\epsilon^8)^2$ redundancy and by arranging the drift tubes in non-orthogonal planes. Furthermore, the system is configured to use tracking residuals 404B for momentum p measurements.

In another alternative embodiment (not shown), a portal monitoring system which is identical to the system 300 of FIG. 11, has drift tubes which are sealed advantageously further to decrease cost and complexity of the system by eliminating the need for a gas handling system.

The aforementioned illustrative embodiments demonstrate that the combination of cosmic ray radiography with passive or active counting therefore provides a robust detector for nuclear threats. Conventional radiography alone is defeated by packaging nuclear material in packages too small to be resolved by the radiography. Passive counting can be defeated by shielding the material with high-z material. The shielding makes the threats move visible radiographically and dispersing the material in many cases enhances the passive signature. Combining these techniques allows one to determine if a given vehicle is free of threats by measuring the absence of a potential shielded package and the absence of a radiation signature.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only.

Other variations and modifications of the present invention will be apparent to those of skill in the art, and it is the intent of the appended claims that such variations and modifications be covered.

The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

What is claimed is:
1. A portal monitoring system comprising
   a cosmic ray charged particle tracker having a plurality of charged particle detectors, said charged particle detectors comprising drift cells configured both to enable tracking of incoming and outgoing charged particles passing through a volume to be scanned and detection of gamma rays and, wherein, in use, said system can both selectively detect any materials or devices occupying said volume from multiple scattering of said charged particles and detect any radioactive sources occupying said volume from gamma rays emitted therefrom.

2. The system of claim 1, wherein said drift cells comprise drift tubes of circular or non-circular cross-section, or non-tube shaped cells.

3. The system of claim 1, wherein said drift cells comprise sealed drift cells.

4. The system of claim 1, wherein an operating gas of said drift cells comprises an non-flammable gas.

5. The system of claim 1, wherein said drift cells comprise a set of drift tubes located above said volume and another set of drift tubes located below said volume, each set of drift tubes having at least three drift tubes configured in a first direction and another at least three drift tubes configured in a second direction.

6. The system of claim 5, wherein said first direction is substantially orthogonal to said second direction.

7. The system of claim 6, wherein said charged particles comprise muons.

8. The system of claim 1, wherein said material comprises a high density material.

9. The system of claim 1, further comprising a gamma ray or neutron source arranged within said system to thereby enable active interrogation of material occupying said volume.

10. A portal monitor system comprising
a cosmic ray muon tomography system having a plurality of muon detectors, said muon detectors comprising drift cells arranged at least above and below a volume to be scanned both to enable tracking of incoming and outgoing muons and counting of gamma rays and, wherein, in use, said system can both selectively detect any high density shielding occupying said volume from multiple scattering of said muons passing through said volume and detect any radioactive material occupying said volume from gamma rays emitted therefrom.

11. The system of claim 10, wherein said drift cells comprise aluminum drift cells or carbon composite drift cells having internal conductive coatings and wherein said drift cells comprise drift tubes of circular or non-circular cross-section, or non-tube shaped cells.

12. The system of claim 11, wherein said operating gas of said drift tube comprises a non-flammable gas.

13. The system of claim 11, wherein said operating gas comprises a mixture of argon and at least one gas selected from the group consisting of carbon dioxide, isobutane, tetrafluoromethane and ethane.

14. The system of claim 11, wherein said drift tubes are arranged in separate planes in two orthogonal coordinates or wherein said drift tubes are arranged in non-orthogonal planes.

15. The system of claim 10, wherein said volume is of sufficient size to enable a vehicle or cargo container to occupy said volume.

16. A method of portal monitoring comprising
arranging a plurality drift cells on opposite sides of a volume to be scanned;
detecting with said drift cells incoming and outgoing cosmic ray charged particles and any gamma rays;
selectively detecting any material occupying said volume from multiple scattering of said charged particles passing through said volume; and
detecting any radioactive sources occupying said volume from detection of said gamma rays.

17. The method of claim 16, wherein said drift cells comprise comprise drift tubes of circular or non-circular cross-section, or non-tube shaped cells.

18. The method of claim 17, wherein said drift cells comprise sealed drift tubes.

19. The method of claim 17, wherein arranging said plurality of drift cells comprises arranging a set of at least three planes of drift tubes above said volume and arranging a set of at least three planes of drift tubes below said volume.

20. The method of claim 16, wherein arranging said plurality of drift cells further comprises arranging said drift tubes in separate planes in two orthogonal coordinates or arranging said drift tubes in non-orthogonal planes.

* * * * *